(12) United States Patent
Jiang et al.

(10) Patent No.: US 11,457,634 B2
(45) Date of Patent: Oct. 4, 2022

(54) S. ROSEOVERTICILLATUS SR-63 AND ITS APPLICATION

(71) Applicant: Zhejiang Normal University, Jinhua (CN)

(72) Inventors: Donghua Jiang, Jinhua (CN); Matida Suwantammarong, Jinhua (CN); Yunzhang Ding, Jinhua (CN); Tingting Shi, Jinhua (CN); Mengxia Lv, Jinhua (CN)

(73) Assignee: ZHEJIANG NORMAL UNIVERSITY, Jinhua (CN)

( * ) Notice: Subject to any disclaimer, the term of this patent is extended or adjusted under 35 U.S.C. 154(b) by 209 days.

(21) Appl. No.: 16/937,322

(22) Filed: Jul. 23, 2020

(65) Prior Publication Data
US 2021/0030010 A1 Feb. 4, 2021

(30) Foreign Application Priority Data

Aug. 1, 2019 (CN) .......................... 201910707928.6

(51) Int. Cl.
*A01N 63/28* (2020.01)
*C12N 1/20* (2006.01)
*C12R 1/465* (2006.01)

(52) U.S. Cl.
CPC ............. *A01N 63/28* (2020.01); *C12N 1/205* (2021.05); *C12R 2001/465* (2021.05)

(58) Field of Classification Search
CPC ... A01N 63/28; C12N 1/205; C12R 2001/465
USPC ....................................................... 424/93.43
See application file for complete search history.

(56) References Cited

FOREIGN PATENT DOCUMENTS

| CN | 85102956 A | 1/1987 |
|---|---|---|
| CN | 108192829 A | 6/2018 |
| CN | 109536543 A | 3/2019 |
| CN | 109576200 A | 4/2019 |

OTHER PUBLICATIONS

Prabavathy et al., Control of blast and sheath blight diseases of rice using antifungal metabolites produced by *Streptomyces* sp. PM5, Biological Control, vol. 39, (2006), pp. 313-319.*
Arshad, Hafiz Muhammad Imran et al., "Pathogenic diversity of Xanthomonas oryzae pv. oryzae isolates collected from Punjab Province of Pakistan", Eur J Plant Pathol, 2017, 147:639-651, 14 pages.
Liu, Qin-ying et al., "Screening & Identification of Endophytic Fungus against Rice White Leaf Blight Xanthomonas oryzae pv. oryzae", Journal of Microbiology, Aug. 2013, vol. 33, No. 4, 5 pages.
Tian, Xiao-wei et al., "Studies on the fungicidal activity of secondary metabolic products of actinomycetes", Plant Protection, vol. 30, No. 2, 2004, 4 pages.
Zhao, Xian-Feng et al., "Field Tests and Analyses of Different Xa 21-transgenic Hybrid Rice Combinations", Acta Agronomica Sinica, vol. 28, No. 4, Jul. 2002, pp. 521-527.
Liu, Yong-feng et al., "Analysis on the resistance of rice varieties (lines) to rice bacterial leaf blight in Jiangsu Province", Plant Protection, vol. 27, No. 5, Oct. 2001, 4 pages.

* cited by examiner

*Primary Examiner* — Jennifer M. H. Tichy

(57) ABSTRACT

The application belongs to the field of biotechnology and microbiology, in particular to a strain of *Streptomyces roseoverticillatus* (Sr-63) which antagonizes the Rice Bacterial Blight and its application in the prevention and treatment of plant diseases. The application discloses a strain of *S. roseoverticillatus* (Sr-63) with the accession number CCTCC No.: M 2019261. It is also disclosed the application of the *S. roseoverticillatus* (Sr-63): used for controlling Rice Bacterial Blight.

1 Claim, 6 Drawing Sheets

Specification includes a Sequence Listing.

FIG. 3

```
GGCTCAGGACGAACCGTCGCCGGCCTGCTTAACACATGCAAGTCGAACGATGAAGCCCTTCGGGTGGATTAGT
GGCGAACGGGTGAGTAGTAACACGTGGGCAATCTGCCCCTGCACTCTGGGACAAGCCCTGAAACGGGGTCTAATACCGG
ATACGACCTTCGAGCGCATGCTTGAAGGTGAAAGCTCCGGCGGTGCAGGATGAGCCCGCGGCCTATCAGCTTGTT
GGTGGGGTGATGGCCTACCAAGGCGACGACGGGTAGCCGGTAGCAGCAGCCCACACTGGGACTGAGAC
ACGGCCCAGACTCCTACGGGAGGCAGCAGTGGGGAATATTGCACAATGGGCGAAAGCCTGATGCAGCGACGCCGCG
TGAGGGATGACGGCCTTCGGGTTGTAAACCTCTTTCAGCAGGGAAGAAGCGAAAGTGACGGTACCTGCAGAAGAAG
CGCCGGCTAACTACGTGCCAGCAGCCGCGGTAATACGTAGGGCGCAAGCGTTGTCCGGAATTATTGGGCGTAAGA
GCTCGTAGGCGGCTTGTCGCGTCGGATGTGAAAGCCCGGGGCTTAACCCCGGGTCTGCATTCGATACGGGCAGGCT
AGAGTTCGGTAGGGGAGATCGGAATTCCTGGTGTAGCGGTGAAATGCGCAGATATCAGGAGGAACACCGGTGGCGA
AGGCGGATCTCTGGGCCGATACTGACGCTGAGGAGCGAAAGCGTGGGGAGCGAACAGGATTAGATACCCTGGTAGT
CCACGCCGTAAACGTTGGGAACTAGGTGTGGGCGACATTCCACGTCGTCCGTGCCGCAGCTAACGCATTAAGTTCCC
CGCCTGGGGAGTACGGCCGCAAGGCTAAAACTCAAAGGAATTGACGGGGGCCCGCACAAGCAGCGGAGCATGTGG
CTTAATTCGACGCAACGCGAAGAACCTTACCAAGGCTTGACATACACCGGAAACGGCCAGAGATGTCTGCCCCCCTTG
TGGTCGGTGTACAGGTGGTGCATGGCTGTCGTCAGCTCGTGTCGTGAGATGTTGGGTTAAGTCCCGCAACGAGCGC
AACCCTTGTCCTGTGTTGCCAGCATGCCCTTCGGGGTGATGGGGACTCACAGGAGACTGCCGGGGTCAACTCGGAG
GAAGGTGGGGACGACGTCAAGTCATCATGCCCCTTATGTCTGGGCTGCACACGTGCTACACGGCCGGTACAATG
AGCTGCGATACCGTGAGGTGGAGCGAATCTCAAAAAGCCGGTCTCAGTTCGGATTGGGGTCTGCAACTCGACCCCA
TGAAGTTGGAGTTGCTAGTAATCGCAGATCAGCATTGCTGCGGTGAATACGTTCCCGGGCCTTGTACACACCGCCCG
TCAAGTCACGAAAGTCGGTAACACCCGAAGCCGGTGGCCCAACCCCTTGTGGGGAGGGAGCCGTCGAAGGTGGGACTGG
CGATTGGGACGAAGTCGTA
```

S. ROSEOVERTICILLATUS SR-63 AND ITS APPLICATION

CROSS REFERENCE TO RELATED APPLICATION

This application claims the priority of Chinese Patent Application No. 201910707928.6, entitled "S. roseoverticillatus Sr-63 and its application" filed with the Chinese Patent Office on Aug. 1, 2019, which is incorporated herein by reference in its entirety.

TECHNICAL FIELD

The invention belongs to the field of biotechnology and microbiology, in particular to a strain of Streptomyces roseoverticillatus (Sr-63) which antagonizes the Rice Bacterial Blight and its application in the prevention and treatment of plant diseases.

BACKGROUND ART

The Rice Bacterial Blight is a major disease of rice, occurs in all rice areas in China, which is caused by Xanthomonas oryzae pv. oryzae, Xoo[1]. The cell is short rod-shaped, 1.0~2.7×0.5~1.0 μm in size, single flagella, polar or subpolar, about 8.7 μm in length, 30 nm in diameter, gram-negative, spore free and capsule free, surrounded by mucinous extracellular polysaccharides. On the artificial medium, the colony is honey yellow, which produces insoluble yellow pigment, aerobic and adopts respiratory metabolism. The optimum growth temperature is 25° C.~30° C., and the optimum pH for growth is 6.5~7.0.

At present, the chemical bactericide beuzole is mainly used to control Rice Bacterial Blight. Due to the problems of chemical bactericide, such as drug residues, environmental pollution, quality and safety of agricultural products, it is of great significance of seeking for microbial strains with antagonistic effect against Rice Bacterial Blight and developing new and efficient microbial bactericide which have the characteristics such as safety and environmental friendliness and are in line with the current concept of green environmental protection.

Actinomycetes are very important microbial resources. Actinomycetes are closely related to people's productions and lives. About 70% of antibiotics widely used are produced by actinomycetes.

Actinomycetes are Gram-positive bacteria with filamentous branching cells, named because the colonies are radial. They are mainly distributed in the form of spores or hyphae in the soil, air and water, especially in the organic rich, neutral or slightly alkaline soil. Actinomycetes like to live in micro-alkaline soil with rich organic matter. The peculiar "muddy smell" of soil is caused by the metabolites of actinomycetes. Actinomycetes are closely related to people's lives. Currently commonly used antibiotic drugs such as streptomycin, oxytetracycline, tetracycline, chloramphenicol, erythromycin, gentamicin are produced by actinomycetes; so far, thousands of antibiotics have been found from microorganisms, of which ⅔ are produced by actinomycetes, which is of great significance in the pharmaceutical industry.

The currently known use of Streptomyces roseoverticillatus is: it can be used in the production of antibiotics for the treatment of acid-fast bacteria such as Mycobacterium tuberculosis.

The currently known uses of Streptomyces are generally: it can be used to antagonize a variety of plant pathogenic fungi such as Colletotrichum gloeosporioides, Botrytis cinerea, Fusarium oxysporum, Gibberella graminearum and Curvularia zeae to produce glutamic acid Gyrase.

For example: Application Number 85102956 "preparation process of antibiotics DO-248-A and DO-248-B" teaches that the antibiotic DO-248-A or DO-248-B can be obtained by culturing Streptomyces roseus. The antibiotic has antibacterial activity against acid resistant bacteria (including Mycobacterium tuberculosis). Application Number 2019100215449 "a recombinant bacterium producing glutamic acid racemase and its construction method and application" teaches: the recombinant bacterium contains MurI gene of glutamic acid racemase of Streptomyces luteus HY61, and uses the glutamic acid racemase fermented by the recombinant bacterium to catalyze the racemization of L-glutamic acid to produce DL-glutamic acid. Application Number 2018100327172 "a kind of Streptomyces luteus and its biological control agents and applications" teaches that: Streptomyces luteus strain HY61 has the advantages of fast sporulation, wide action spectrum to prevent and control various plant diseases, strong genetic stability, good compatibility with the environment, long disease control duration and so on. Plant diseases include Colletotrichum gelatinosum, Botrytis cinerea, Fusarium oxysporum, Gibberella tritici and Curvularia zeamais. Application Number 2018115899615, a method for preparing carbazomycin B by microbial fermentation, Streptomyces luteoverticillatus strain HY61, discusses a microbial fermentation method for preparing carbazomycin B.

SUMMARY OF THE INVENTION

The technical problem to be solved by the application is to provide a strain of S. roseoverticillatus (Sr-63) and its application.

In order to solve the above technical problem, the application provides a strain of S. roseoverticillatus (Sr-63) with the accession number CCTCC No.: M 2019261.

It is also provided the application of the S. roseoverticillatus (Sr-63) strain: for controlling Rice Bacterial Blight.

The depository information of S. roseoverticillatus (Sr-63) strain of the present application is as follows: deposit name: Streptromyces roseoverticillatus (Sr-63), depository institution: China Center for Type Culture Collection, depository address: Wuhan University, China, accession number CCTCC No.: M 2019261, deposit date: Apr. 15, 2019. The present application is directed to the problems of chemical control of Rice Bacterial Blight and the increasing harm of agriculture control, and uses microorganisms and their secondary metabolites to carry out biological control of Rice Bacterial Blight, thereby providing a S. roseoverticillatus (Sr-63) strain with high antagonism against bacterial blight. Streptromyces roseoverticillatus (Sr-63) strain is selected from rhizosphere soil of Ophiopogon bodinieri. According to its morphological characteristics and 16S rRNA gene sequence, S. roseoverticillatus is identified.

S. roseoverticillatus (Sr-63) strain can be used to control Rice Bacterial Blight; the fermentation filtrate of S. roseoverticillatus (Sr-63) strain has significant inhibitory effect on Rice Bacterial Blight. Under the condition of initial pH 6.5-7.5 of fermentation medium and culture temperature of 28° C., after 5 days of liquid fermentation, the diameter of bacteriostatic circle of fermentation filtrate to Xanthomonas oryzae pv. oryzae can reach 45 mm-55 mm (FIG. 5).

The results of antimicrobial spectrum test show that the fermentation filtrate of S. roseoverticillatus (Sr-63) is resistant to four representative plant pathogenic fungi: *Fusarium solani, Gibberella fujikuroi, Fusarium oxysporum* f sp. *momordicae, Alternaria solani*. The inhibition rates of four representative plant pathogenic fungi respectively are 12.62%, 11.02%, 9.44% and 7.43%. It can also inhibit four representative plant pathogenic bacteria: *Xanthomonas oryzae* pv. *oryzicola, Xanthomonas campestris* pv. *glycines, Xanthomonas campestris* pv. *vesicatoria, Pseudomonas syringae* pv. *glycinea*.

The fermentation filtrate of S. roseoverticillatus (Sr-63) has significant effect on the control of Rice Bacterial Blight. When the initial pH is 6.5~7.5 of fermentation medium and the culture temperature is 28° C., the control effect of fermentation filtrate on Rice Bacterial Blight can reach 80%~95% after 7 days of liquid fermentation. S. roseoverticillatus (Sr-63) is a useful strain of microbial bactericide, which has a good prospect in biological control of Rice Bacterial Blight. However, existing S. roseoverticillatus, such as BNCC152383 S. roseoverticillatus AB 184715 fermentation filtrate did not show the control effect on Rice Bacterial Blight.

BRIEF DESCRIPTION OF THE DRAWINGS

FIG. 3 shows the 16S rRNA gene sequence of S. roseoverticillatus (Sr-63) (1461 bp).

Note: A is the control, with the addition of sterile water; B is the fermentation filtrate of S. roseoverticillatus (Sr-63).

Figure 6:
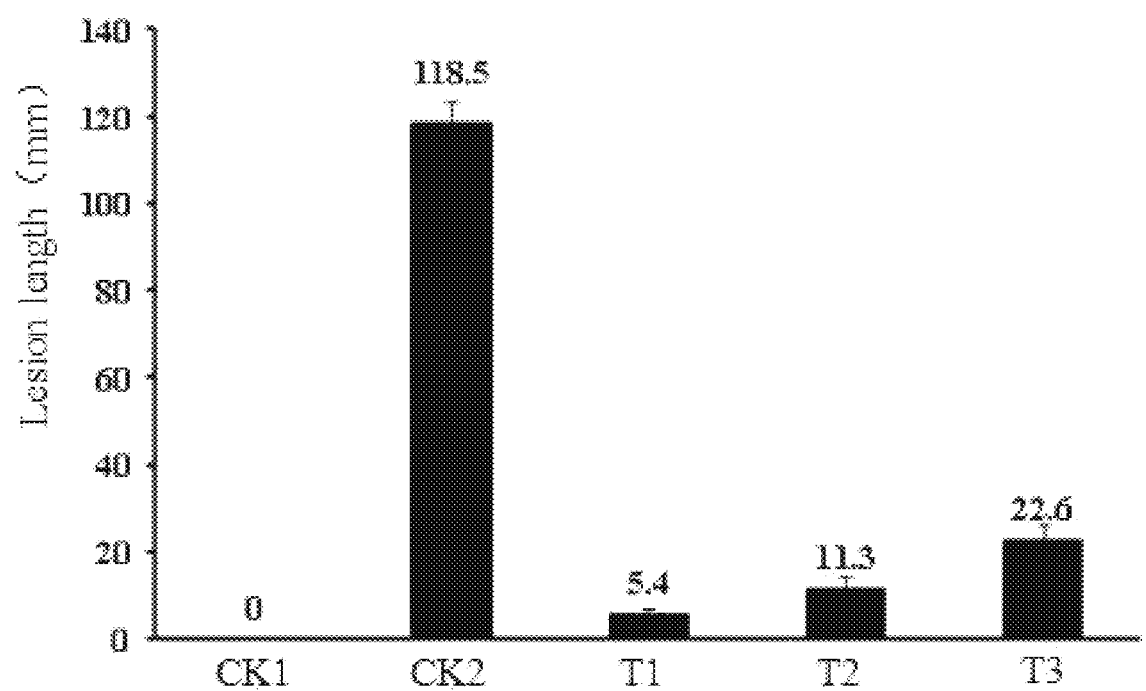

FIG. 6 shows the effect of the fermentation filtrate of S. roseoverticillatus (Sr-63) on the control of Rice Bacterial Blight.

DETAILED DESCRIPTION OF THE EMBODIMENTS

The invention will be further described in combination with specific embodiments, but the scope of protection of the invention is not limited thereto.

Example 1

Isolation, Purification, Screening and Identification of S. Roseoverticillatus

1. Strain (1) Actinomycetes: actinomycetes from different habitats of soil (e.g. paddy field, lawn, tomato field, potato field, *Ophiopogon japonicus* field, etc.) are isolated, purified, screened and identified, and preserved for identification.

(2) P6 race of *Xanthomonas oryzae* pv. *oryzae*.

2. Medium (1) The solid medium of Gauze's Medium No. 1: soluble starch 20 g, $KNO_3$ 1 g, $K_2HPO_4$ 0.5 g, $MgSO_4 \cdot 7H_2O$ 0.5 g, NaCl 0.5 g, $FeSO_4 \cdot 7H_2O$ 0.01 g, agar 20 g, water 1000 ml, pH 7.2~7.4. It is used for isolation, purification and identification of actinomycetes.

(2) The liquid medium of Gauze's Medium No. 1: the formula is the same as (1) without agar; it is used for liquid fermentation of actinomycete strains.

(3) The solid medium of *Xanthomonas oryzae* pv. *oryzae*, Xoo (Xoo solid medium): potato 300 g, sucrose 15 g, Ca$(NO_3)_2$ 0.5 g, $NaH_2PO_4 \cdot 12H_2O$ 2.0 g, tryptone 5.0 g, agar 20 g, water 1000 ml, pH 6.5. It is used for solid culture of P6 race of *Xanthomonas oryzae* pv. *oryzae*.

(4) The liquid medium of *Xanthomonas oryzae* pv. *oryzae*, Xoo (Xoo culture medium): the formula is without agar, and the rest is the same as (3); it is used for fermentation of P6 race of *Xanthomonas oryzae* pv. *oryzae*.

3. Experimental Method 3.1 Isolation, Purification and Preservation of Actinomycetes 1 g natural air-dried soil sample (moisture content≤3%) was taken to put into 99 ml sterile water and shaken on a shaker at 120 r/min for 30 min. The supernatant was diluted by gradient ($10^{-2}$~$10^{-5}$), and 100 μl of the supernatant was evenly coated on Gauze's Medium No. 1 at a suitable concentration ($10^{-3}$). The supernatant was cultured in a 28° C. incubator for 48 hours until the colony appeared. A single colony with typical actinomycete colony characteristics was selected and transferred to another Gauze's Medium No. 1, and the pure strain was obtained after three times of scribing purification; the strain was numbered and stored in a refrigerator at 4° C. for standby.

3.2 Screening of Actinomycetes Against Bacterial Blight of Rice 3.2.1 Preliminary Screening of Co Culture Method The P6 race of *Xanthomonas oryzae* pv. *oryzae* was inoculated into Xoo culture medium and activated on shaking table (180 r/min, 28° C.). When the bacterial density reached $OD_{600}$ of 0.6, 100 μl bacterial solution was evenly coated on Xoo solid culture medium. The activated actinomycete cake (diameter 4 mm) was inoculated in the middle of Xoo solid culture medium, cultured at 28° C. for 48 hours, and the bacteriostatic circle was observed. The antagonistic actinomycetes were screened according to the existence and size of bacteriostatic circle and preserved with 25% glycerol.

3.2.2 Oxford Cup Screen (1) Fermentation of actinomycetes: The antagonistic actinomycete strains were inoculated into Gauze's Medium No. 1 plate and cultured in 28° C. incubator for 3 days; The actinomycete cake was made by a 4 mm punch and inoculated into a 250 ml conical flask filled with 100 ml liquid medium of Gauze's Medium No. 1 and cultured on shaking table (160 r/min, 28° C.) for 5 days. The fermentation liquid was placed in a 50 ml centrifuge tube for 12000 r/min and centrifuged for 10 minutes. The supernatant was filtered with 0.22 μm organic filter membrane to remove the residual spores and obtain the fermentation filtrate. (2) Culture of the P6 race of *Xanthomonas oryzae* pv. *oryzae: P6* race of *Xanthomonas oryzae* pv. *oryzae* was inoculated in Xoo culture medium, which was activated on shaking table (180 r/min, 28° C.). When the density of bacteria reached $OD_{600}$ of 0.6, 100 μl of bacteria solution was evenly coated on Xoo solid culture medium. An Oxford cup method was applied to 200 μl of fermentation filtrate of actinomycetes to determine the inhibition of each actinomycetes on P6 race of *Xanthomonas oryzae* pv. *oryzae*. The actinomycetes with strong antagonistic effect were selected according to the size of bacteriostatic circle.

3.3 Identification of Actinomycete Target Strains Against Rice Bacterial Blight

A small amount of mycelium of actinomycetes target strain was picked out with tweezers and transferred to Gauze's Medium No. 1 plate, for an activate culture for 3 days; The actinomycete cake (with a diameter of 4 mm) was inoculated on the new Gauze's Medium No. 1 plate and cultured at 28° C. for 5 days, the morphological characteristics of the substrate mycelium, aeromycelium and spore hyphae were observed with microscope, and photographed.

The genomic DNA of the target strain was extracted, the 16S rRNA gene was amplified and sent to Sangon Biotech (Shanghai) Co., Ltd for sequencing. The 16S rRNA gene sequence obtained by sequencing was submitted to GenBank and analyzed by blast comparison to determine the type of actinomycete.

Figure 1:
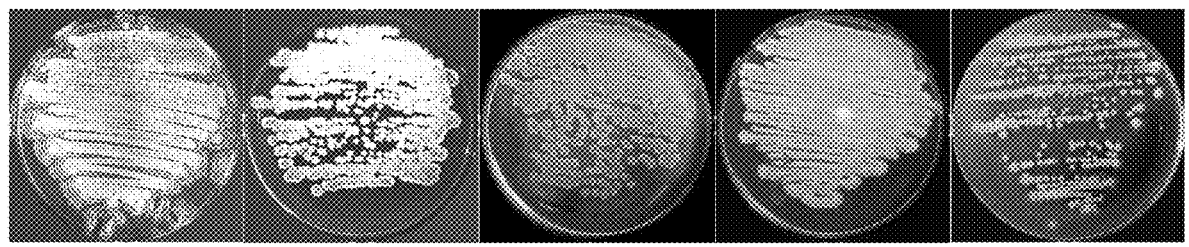
FIG. 1 shows the schematic diagram of the colonies (Gauze's Medium No. 1, 5 days) of 5 representative pure actinomycetes strains. From left to right, Sr-4; Sr-15; Sr-32; Sr-38; Sr-63.

4. Experimental Results 4.1 Acquisition of Pure Actinomycetes 65 pure strains of actinomycetes were isolated and purified from soil samples of different habitats. The colonies of 5 representative pure strains of actinomycetes cultured in Gauze's Medium No. 1 for 5 days are shown in FIG. 1.

4.2 Screening of Actinomycetes Against Bacterial Blight of Rice 65 strains of actinomycetes were screened by co-culture method and Oxford cup method. The results show that different strains of actinomycetes have different inhibition on bacterial blight. One actinomycete strain, Sr-63 strain, with a diameter of 50 mm, was isolated from the rhizosphere soil of *Ophiopogon bodiieri*.

4.3 Identification Results of Actinomycete Sr-63

Figure 2:
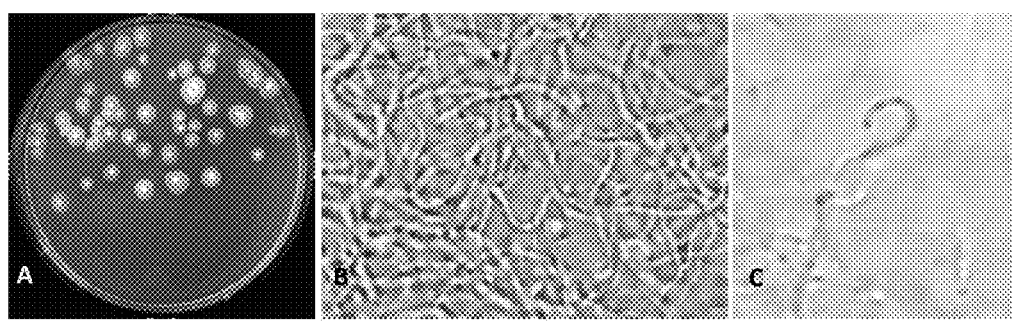
FIG. 2 shows the colony (A), substrate hyphae (B) and spore hyphae (C) of S. roseoverticillatus (Sr-63) cultured on Gauze's Medium No. 1 for 5 days.

Morphological characteristics of strain Sr-63: cultured at 28° C. for 5 days on Gauze's Medium No. 1, the colony is small and the surface is pink velvet; under the microscope, the mycelia in the substrate and aerial mycelia are branched and slender, mature aerial mycelium forms polysporic chain, and the spore hyphae is open-loop (FIG. 2). The results of physiological and biochemical tests show: gram staining is positive; It uses glucose, hydrolyzes gelatin and starch, and is aerobic. Glucose, raffinose, rhamnose, mannose, mannitol and α-lactose can be used as carbon sources. Preferable nitrogen sources are peptone and $KNO_3$. The suitable concentration of NaCl is 0.5~1%, pH is 6.5~7.5, and the culture temperature is 28° C.

Figure 4:
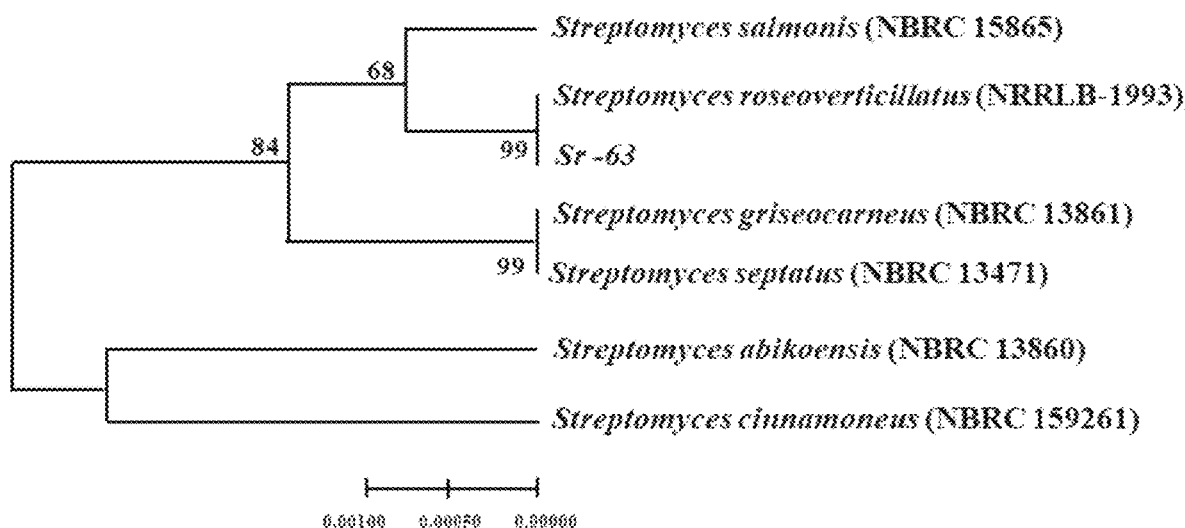
FIG. 4 shows the phylogenetic tree of S. roseoverticillatus (Sr-63) based on 16S rRNA gene sequence.
Figure 5:
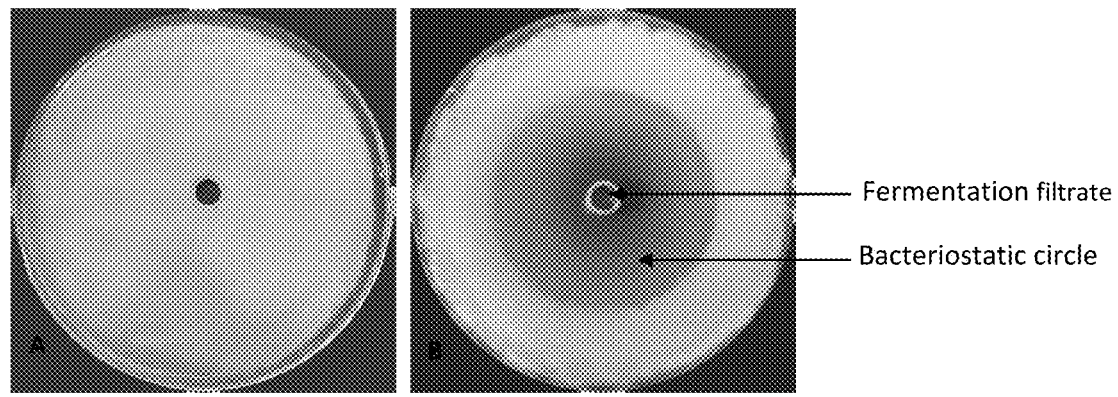
FIG. 5 shows the inhibition circle of S. roseoverticillatus (Sr-63) fermentation filtrate to P6 race of *Xanthomonas oryzae* pv. *oryzae*.

Sequence analysis of 16S rRNA gene: the result shows that its length is 1461 bp (FIG. 3, SEQ ID NO.1), which is closest to the evolutionary distance of *Streptomyces roseoverticillatus* (FIG. 4), and the similarity is 99%.

According to the morphological characteristics of strain Sr-63, combined with the key list of *Streptomyces*, strain Sr-63 was identified as *Streptomyces roseoverticillatus*.

The Sr-63 strain was deposited, and the depository information is as follows: deposit name: *Streptomyces roseoverticillatus* Sr-63, depository institution: China Center for Type Culture Collection, depository address: Wuhan University, Wuhan, China, accession number CCTCC No.: M 2019261, deposit date Apr. 15, 2019.

Example 2

Determination of the Antibacterial Spectrum of the Fermentation Broth of *S. Roseoverticillatus* Sr-63

1. Strain (1) *S. roseovarticulatus* Sr-63 strain.

(2) Four representative plant pathogenic fungi: *Fusarium solani, Gibberella fujikuroi, Fusarium oxysporum* f sp. *momordicae* and *Alternaria solani* were used to test the antimicrobial spectrum of the fermentation broth of Sr-63 strain against plant pathogenic fungi.

(3) Four representative plant pathogenic bacteria: *Xanthomonas oryzae* pv. *oryzicola, Xanthomonas campestris* pv. *glycines, Xanthomonas campestris* pv. *vesicatoria,* and *Pseudomonas suringae* pv. *glycinea* were used to test the antimicrobial spectrum of the fermentation broth of Sr-63 strain against plant pathogenic bacteria.

2. Medium (1) PDA medium: potato 200 g, glucose 20 g, agar 20 g, water 1 L, pH 6.0~6.5. It was used to culture four kinds of plant pathogenic fungi.

(2) Beef extract peptone medium: beef extract 3 g, peptone 10 g, NaCl 5 g, with water added to 1000 ml, pH adjusted to 7.5 (beef extract peptone agar medium was added with 18 g agar powder). It was used for the culture of four plant pathogenic bacteria.

(3) Gauze's Medium No. 1 was used for the fermentation seed culture of *Streptomyces* Sr-63.

(4) Gauze's Medium No. 1 was used for the fermentation of *Streptomyces* Sr-63.

3 Experimental Method 3.1 Activation and Culture of Plant Pathogenic Fungi

Four pathogenic fungi stored at 4° C. were inoculated in PDA medium and activated at 28° C. for 2 days. Then they were transferred to a new PDA medium and cultured at 28° C. for 4 days to determine the antifungal spectrum.

3.2 Activation and Culture of Plant Pathogenic Bacteria

Four plant pathogenic bacteria stored at 4° C. were inoculated in beef extract peptone medium and activated at 28° C. for 2 days. Then they were transferred to a new beef extract peptone medium and cultured at 28° C. for 2 days to determine the antibacterial spectrum.

3.3 Determination of Antimicrobial Spectrum of *Streptomyces* Sr-63

(1) Preparation of Fermentation Filtrate of *Streptomyces* Sr-63

The *S. roseoverticillatus* (Sr-63) was inoculated into the medium plate of Gauze's Medium No. 1, and cultured in a 28° C. incubator for 4 days. A cake of *S. roseoverticillatus* (Sr-63) was taken from a 4 mm punch and inoculated into a 250 ml conical flask filled with 40 ml Gauze's Medium No. 1, it was shaken on a shaking table for 5 days (160 r/min, 28° C.). The fermentation solution was placed in a 50 ml centrifuge tube at 12000 r/min for 10 minutes. The supernatant was filtered by 0.22 μm organic filter membrane to remove the residual spores and obtain the fermentation filtrate for standby.

(2) Determination of Antifungal Spectrum of Plant Pathogens

The fermentation filtrate was mixed with PDA solid medium at 50° C. with a volume ratio of 1:9, then poured into the culture dish to obtain a plate containing the fermentation filtrate. A 6 mm diameter cake with 4 plant pathogenic fungi to be tested was placed in the center of the plate. It was cultured at 28° C. for 72 hours. The diameter of four plant pathogenic fungi was measured by cross method. Three groups of parallel repeats were conducted and the average value was taken. The inhibition rate of mycelium growth was calculated according to the following formula.

Mycelium growth inhibition rate %=(diameter of the control colony—diameter of the treated colony)/ (diameter of the control colony −6)×100

(3) Determination of Antibacterial Spectrum of Plant Pathogens

Four plant pathogenic bacteria were inoculated into beef extract peptone medium respectively, and were activated on shaking table (180 r/min, 28° C.). When the bacterial density reached $OD_{600}$ of 0.6, 100 µl bacterial solution was coated on the solid medium of beef extract peptone. The inhibition of the fermentation broth of 200 µL S. roseoverticillatus (Sr-63) on the four plant pathogenic bacteria was determined by the Oxford cup method.

4. Experimental Results 4.1 Inhibition of Streptomyces Sr-63 on Four Plant Pathogenic Fungi The results show that the fermentation broth of S. roseoverticillatus (Sr-63) has certain inhibitory effect on four plant pathogenic fungi. The mycelial growth inhibition rates of Fusarium solani, Gibberella fujikuroi, Fusarium oxysporum f.sp. momordicae and Alternaria solani respectively were 12.62%, 11.02%, 9.44% and 7.43% (Table 1).

TABLE 1

Inhibitory effect of fermentation filtrate of S. roseoverticillatus (Sr-63) on four plant pathogenic fungi

| Pathogenic fungi | Mycelium growth inhibition rate (%) |
|---|---|
| Fusarium solani | 12.62 ± 1.56 |
| Gibberella fujikuroi | 11.02 ± 1.35 |
| Fusarium oxysporum f. sp. momordicae | 9.44 ± 1.16 |
| Alternaria solani | 7.43 ± 0.89 | note:
Mycelium growth inhibition rate (%) = (diameter of the control colony − diameter of the treated colony)/(diameter of the control colony − 6) × 100

4.2 Inhibition of Fermentation Filtrate of S. Roseoverticillatus (Sr-63) on the Four Plant Pathogenic Bacteria The results show that the fermentation filtrate of S. roseoverticillatus (Sr-63) has some inhibition on four representative plant pathogenic bacteria, among which the inhibition on Xanthomonas oryzae pv. oryzicola was relatively good (Table 2), and diameter of bacteriostatic circle was about 28 mm.

TABLE 2

Inhibitory effect of fermentation filtrate of S. roseoverticillatus (Sr-63) on the four plant pathogenic bacteria

| Plant pathogenic bacteria | Diameter of bacteriostatic circle (mm) |
|---|---|
| Xanthomonas oryzae pv. oryzicola | 28.33 ± 3.96 |
| Xanthomonas campestris pv. glycines | 21.50 ± 2.81 |
| Xanthomonas campestris pv. vesicatoria | 18.50 ± 1.73 |
| Pseudomonas syringae pv. glycinea | 15.50 ± 1.47 |

Example 3

Study on the Control Effect of the Fermentation Liquid of S. Roseoverticillatus (Sr-63) on Rice Bacterial Blight 1. Pathogens and Rice Strains Pathogen: P6 race of Xanthomonas oryzae pv. oryzae.

Rice strain: Zhonghua 11 rice strain susceptible to P6 race of Xanthomonas oryzae pv. oryzae.

2. Experimental Method 2.1 Preparation of Fermentation Filtrate of S. Roseoverticillatus (Sr-63): the Method is the Same as Eexample 2.

2.2 The Control Effect of Fermentation Filtrate of S. Roseoverticillatus (Sr-63) on Rice Bacterial Blight According to the methods in the references[2,3], the leaves of Zhonghua 11 rice line were treated by the fermentation filtrate of S. roseoverticillatus (Sr-63); the inoculation of the P6 race of Xanthomonas oryzae pv. oryzae suspension and the statistics of disease were according to the methods of references [4,5].

(1) Preparation of P6 race of Xanthomonas oryzae pv. oryzae suspension: P6 race of Xanthomonas oryzae pv. oryzae suspension was inoculated on Xoo solid medium by plate scribing method and activated for 48 h; One ring of P6 race of Xanthomonas oryzae pv. oryzae suspension was inoculated into Xoo solid medium by scraping with inoculating ring and cultured on shaking bed at 28° C. and 180 r/min for 48 h. When the OD value reached 0.6, it was ready for use.

(2) Method of inoculating P6 race of Xanthomonas oryzae pv. oryzae into rice leaves: when the rice grows to tillering stage, the rice leaf tip was horizontally cut off by 1.5 cm with a pair of scissors sterilized and dipped in P6 race of Xanthomonas oryzae pv. oryzae suspension[4,5].

(3) Experimental design of controlling Rice Bacterial Blight: in the experiment, the distilled water blank control group (CK1), the P6 race of Xanthomonas oryzae pv. oryzae suspension treatment control group (CK2), method 1 treated group (treatment 1), method 2 treated group (treatment 2) and method 3 treated group (treatment 3) were set.

a:CK1: the sterilized scissors were dipped in the distilled water, then the leaves were cut by the scissors, and the inoculated parts were kept moist.

b:CK2: the sterilized scissors were dipped in the suspension of P6 race of Xanthomonas oryzae pv. oryzae, then the leaves were cut by the scissors, and the inoculated parts were kept moist.

c:T1(treatment 1): the fermented filtrate of S. roseoverticillatus (Sr-63) was first sprayed with a watering can, according to the amount of 1 ml/cm² fermented filtrate every 1 hour, three times in total. After 12 hours, P6 race of Xanthomonas oryzae pv. oryzae suspension was inoculated according to the method of control group (CK2), and the inoculated part was kept moist.

d: T2(treatment 2): the leaves were cut and inoculated with P6 race of Xanthomonas oryzae pv. oryzae suspension, and 6 hours after the fermentation filtrate of S. roseoverticillatus (Sr-63) was sprayed; the method, the amount of fermentation filtrate and moisture retention were the same as treatment 1.

e:T3(treatment 3): the leaves were cut and inoculated with P6 race of Xanthomonas oryzae pv. oryzae suspension, and 12 hours after the fermentation filtrate of S. roseoverticillatus (Sr-63) was sprayed; the method, the amount of fermentation filtrate and moisture retention were the same as treatment 1.

After the occurrence and development of rice leaf lesions have stabilized, record and count the incidence. The lesion inhibition rate was calculated.

Lesion inhibition rate (%)=(lesion length of the CK2—lesion length of the treated)/lesion length of the CK2×100

3. Experimental Results of Control Effect of Different Treatments on Rice Bacterial Blight The lengths of Rice Bacterial Blight lesions measured by different treatment methods are shown in FIG. 6, no lesions were found in the distilled water blank control group (CK1); the average length of the lesions in the P6 race suspension treatment control group (CK2) was 118.5 mm; the average length of the lesions in T1, T2 and T3 respectively were 5.4 mm, 11.3 mm and 22.6 mm. Inhibition rate of lesions in Zhonghua 11 rice lines in the T1, T2 and T3 were respectively 95.4%, 90.5% and 80.9%.

The results show that the fermentation filtrate of *S. roseoverticillatus* (Sr-63) has a significant effect on the control of Rice Bacterial Blight in Zhonghua 11 rice strain susceptible to P6 race of *Xanthomonas oryzae* pv. *oryzae*. The earlier spraying, the better the effect of disease prevention.

The following references, which are mentioned above, are incorporated by reference herein in their entirety:

[1] Arshad H M I, Saleem K, Khan J A, et al. Pathogenic diversity of *Xanthomonas oryzae* pv. *oryzae* isolates collected form Punjab Province of Pakistan [J]. European Journal of Plant Pathology, 2017, 147(3): 639-651. (Arshad H M I, Saleem K, Khan J A, et al.;

[2] Liu Qinying, Xie Xiangcong, QiYuping, et al. Screening & Identification of Endophytic Fungus against Rice White Leaf Blight *Xanthomonas oryzae* pv. *oryzae* [J]. Journal of Microbiology, 2013, 33(4): 4-8;

[3] Tian Xiaowei, Long Jianyou, Bai Hongjin, et al. Studies on Fungicidal Activity of Metabolic Products of Actinomycetes[J]. Plant Protection, 2004, 30(2): 51-54;

[4] Zhao Xianfeng, Zhai Wenxue, Li Ping, et al. Field Tests and Analyses of Different Xa21-transgenic Hybrid Rice Combinations[J]. Acta Agronomica Sinica, 2002, 28(4): 521-527; and

[5] Liu Yongfeng, Lu Fan, Chen Zhiyi, et al. Analysis on the Resistance of Rice Varieties (lines) to Rice Bacterial Leaf Blight in Jiangsu Province[J]. Plant Protection, 2001, 5: 3-6.

Contrast

The rest of *Streptomyces roseoverticillatus* obtained in the process of the application is detected according to the method described in treatment 1 of example 3 above, and the results are compared with that of *S. roseoverticillatus* (Sr-63) of the application, as shown in Table 3 below:

TABLE 3

| Strain | Source | Lesion length (mm) |
|---|---|---|
| Sr-63 | Screening by the application | 5.4 |
| Sr-4 | Screening by the application | 40.8 |
| Sr-38 | Screening by the application | 55.2 |

Finally, it should be noted that the above listed are only a few of specific embodiments of the present application. Obviously, the present application is not limited to the above embodiments, and there can be many variations. All variations that can be directly derived from or associated with the contents of the disclosure by those skilled in the art shall be considered as the protection scope of the present invention.

What is claimed is:

1. A method for controlling Rice Bacterial Blight, comprising administering an *S. roseoverticillatus* strain to rice in need thereof, wherein the *S. roseoverticillatus* strain is *Streptomyces roseoverticillatus* Sr-63 strain with accession number CCTCC No.: M 2019261.

\* \* \* \* \*

SEQUENCE LISTING

```
<160> NUMBER OF SEQ ID NOS: 1

<210> SEQ ID NO 1
<211> LENGTH: 1461
<212> TYPE: DNA
<213> ORGANISM: Streptomyces roseoverticillatus Sr-63

<400> SEQUENCE: 1
ggctcaggac gaacgctggc ggcgtgctta acacatgcaa gtcgaacgat gaagcccttc     60
ggggtggatt agtggcgaac gggtgagtaa cacgtgggca atctgccctg cactctggga    120
caagccctgg aaacggggtc taataccgga tacgaccttc gagcgcatgc ttgaaggtgg    180
aaagctccgg cggtgcagga tgagcccgcg gcctatcagc ttgttggtgg ggtgatggcc    240
taccaaggcg acgacgggta gccggcctga gagggcgacc ggccacactg ggactgagac    300
acggcccaga ctcctacggg aggcagcagt ggggaatatt gcacaatggg cgaaagcctg    360
atgcagcgac gccgcgtgag ggatgacggc cttcgggttg taaacctctt tcagcaggga    420
agaagcgaaa gtgacggtac ctgcagaaga agcgccggct aactacgtgc cagcagccgc    480
ggtaatacgt agggcgcaag cgttgtccgg aattattggg cgtaaagagc tcgtaggcgg    540
cttgtcgcgt cggatgtgaa agcccggggc ttaaccccgg gtctgcattc gatacgggca    600
ggctagagtt cggtagggga gatcggaatt cctggtgtag cggtgaaatg cgcagatatc    660
aggaggaaca ccggtggcga aggcggatct ctgggccgat actgacgctg aggagcgaaa    720
gcgtggggag cgaacaggat tagataccct ggtagtccac gccgtaaacg ttgggaacta    780
ggtgtgggcg acattccacg tcgtccgtgc cgcagctaac gcattaagtt ccccgcctgg    840
ggagtacggc cgcaaggcta aaactcaaag gaattgacgg gggcccgcac aagcagcgga    900
```

-continued

```
gcatgtggct taattcgacg caacgcgaag aaccttacca aggcttgaca tacaccggaa     960
acggccagag atggtcgccc ccttgtggtc ggtgtacagg tggtgcatgg ctgtcgtcag    1020
ctcgtgtcgt gagatgttgg gttaagtccc gcaacgagcg caacccttgt cctgtgttgc    1080
cagcatgccc ttcggggtga tggggactca caggagactg ccggggtcaa ctcggaggaa    1140
ggtggggacg acgtcaagtc atcatgcccc ttatgtcttg ggctgcacac gtgctacaat    1200
ggccggtaca atgagctgcg ataccgtgag gtggagcgaa tctcaaaaag ccggtctcag    1260
ttcggattgg ggtctgcaac tcgaccccat gaagttggag ttgctagtaa tcgcagatca    1320
gcattgctgc ggtgaatacg ttcccgggcc ttgtacacac cgcccgtcac gtcacgaaag    1380
tcggtaacac ccgaagccgg tggcccaacc cttgtggagg gagccgtcga aggtgggact    1440
ggcgattggg acgaagtcgt a                                              1461
```